United States Patent
Maalouf

(10) Patent No.: US 10,184,970 B2
(45) Date of Patent: Jan. 22, 2019

(54) CONNECTOR MATING ASSURANCE SYSTEM AND METHOD

(71) Applicant: TYCO ELECTRONICS CORPORATION, Berwyn, PA (US)

(72) Inventor: Khalil John Maalouf, Chambersburg, PA (US)

(73) Assignee: TE CONNECTIVITY CORPORATION, Berwyn, PA (US)

( * ) Notice: Subject to any disclaimer, the term of this patent is extended or adjusted under 35 U.S.C. 154(b) by 505 days.

(21) Appl. No.: 14/877,055

(22) Filed: Oct. 7, 2015

(65) Prior Publication Data

US 2017/0102423 A1    Apr. 13, 2017

(51) Int. Cl.
*H04R 29/00* (2006.01)
*G01R 31/04* (2006.01)
*H01R 13/502* (2006.01)
*H01R 13/641* (2006.01)
*H01R 43/26* (2006.01)

(52) U.S. Cl.
CPC ......... *G01R 31/045* (2013.01); *H01R 13/502* (2013.01); *H01R 13/641* (2013.01); *H01R 43/26* (2013.01)

(58) Field of Classification Search
None
See application file for complete search history.

(56) References Cited

U.S. PATENT DOCUMENTS

| | | | | |
|---|---|---|---|---|
| 7,530,821 | B2 * | 5/2009 | Miyake | G09F 3/10 29/873 |
| 8,186,216 | B2 | 5/2012 | Ogawa et al. | |
| 8,981,961 | B2 * | 3/2015 | Benner | G08B 21/18 340/870.1 |
| 2007/0008152 | A1 | 1/2007 | Parias | |

(Continued)

FOREIGN PATENT DOCUMENTS

| | | |
|---|---|---|
| DE | 10308403 A1 | 9/2004 |
| EP | 2161796 A1 | 3/2010 |

(Continued)

OTHER PUBLICATIONS

Yukinobu JP 2008-226506 (hereinafter Yukinobu; English Machine Translation submitted by Applicant; Published Sep. 25, 2008).*

(Continued)

*Primary Examiner* — Farhana Hoque

(57) ABSTRACT

A connector mating assurance system includes an audible sensor configured to be located in a vicinity of a mating zone for electrical connectors. The audible sensor is configured to detect an audible sound when the electrical connectors are mated. The system includes a connector identification sensor configured to be located in the vicinity of the electrical connectors. The connector identification sensor is configured to identify the presence of the electrical connectors. The system includes a controller connected to the audible sensor and the connector identification sensor. The controller receives connector identification signals from the connector identification sensor and the controller receives audio (Continued)

signals from the audible sensor. The controller processes the connector identification signals and the audio signals for mating assurance.

21 Claims, 3 Drawing Sheets

(56) References Cited

U.S. PATENT DOCUMENTS

| | | | | |
|---|---|---|---|---|
| 2009/0047824 A1* | 2/2009 | Seibert | ............... | H01R 13/641 439/490 |
| 2009/0310795 A1 | 12/2009 | Apsey et al. | | |
| 2010/0242599 A1 | 9/2010 | Ogawa et al. | | |
| 2013/0114824 A1* | 5/2013 | Wu | ............... | H04R 3/12 381/74 |
| 2013/0267120 A1* | 10/2013 | Rothkopf | ............... | H01R 13/64 439/620.21 |
| 2015/0098574 A1 | 4/2015 | Fry et al. | | |

FOREIGN PATENT DOCUMENTS

| | | |
|---|---|---|
| JP | 03297080 A | 12/1991 |
| JP | H04370673 A | 12/1992 |
| JP | 07185952 A | 7/1995 |
| JP | 2006-221971 A | 8/2006 |
| JP | 2007-004073 A | 1/2007 |
| JP | 2008-226506 A | 9/2008 |

OTHER PUBLICATIONS

International Search Report, International Application No. PCT/US2016/050617, International Filing Date, Sep. 8, 2016.

International Search Report, International Application No. PCT/US2014/057085, International Filing Date, Sep. 24, 2014.

Fujitsu Laboratories Ltd., "Fujitsu Develops Glove-Style Wearable Device"; Touch- and gesture-based input supports field work, Feb. 18, 2014, 4 pgs.

* cited by examiner

CONNECTOR MATING ASSURANCE SYSTEM AND METHOD

BACKGROUND OF THE INVENTION

The subject matter herein relates generally to connector mating assurance systems and methods.

Ensuring that mating pairs of electrical connectors are mated properly is important in electrical systems, particularly in electrical systems that exhibit vibration during operation, such as in automotive applications. For example, an electrical connector can be partially mated during a car assembly process, such as in a car assembly factory, and can pass conventional electrical assurance tests, such as tests that pass electrical signals through the electrical connectors to determine electrical connection of the connectors. However, once in operation, the car vibration can cause the electrical connectors to come loose and cause failure.

Conventional assembly methods for electrical connectors provide a mating mechanism, such as a latch, that produces a click when the latch latches in place. However, in an assembly situation, a worker may not properly hear the click due to background factory noises, or could confuse the click with other sounds that closely resemble a connector click. Some known systems use a double casing of the connector, where a second case only fits if the electrical connectors were properly mated. However, such systems have increased cost associated with the second case and increased labor time to assemble.

A need remains for a connector mating assurance system and method to detect proper mating of electrical connectors.

BRIEF DESCRIPTION OF THE INVENTION

In one embodiment, a connector mating assurance system is provided including an audible sensor configured to be located in a vicinity of a mating zone for electrical connectors. The audible sensor is configured to detect an audible sound when the electrical connectors are mated. The system includes a connector identification sensor configured to be located in the vicinity of the electrical connectors. The connector identification sensor is configured to identify the presence of the electrical connectors. The system includes a controller connected to the audible sensor and the connector identification sensor. The controller receives connector identification signals from the connector identification sensor and the controller receives audio signals from the audible sensor. The controller processes the connector identification signals and the audio signals for mating assurance.

In another embodiment, a connector mating assurance system is provided including a user worn sensor unit configured to be worn on or near a user's hand. The user worn sensor unit includes an audible sensor and a connector identification sensor configured to be positioned in a vicinity of a mating zone for electrical connectors. The audible sensor is configured to detect an audible sound when the electrical connectors are mated. The connector identification sensor is configured to identify the presence of the electrical connectors. The system also includes a controller connected to the audible sensor and the connector identification sensor. The controller receives connector identification signals from the connector identification sensor. The controller receives audio signals from the audible sensor. The controller processes the connector identification signals and the audio signals for mating assurance.

In a further embodiment, a method of detecting electrical connector mating is provided including positioning an audible sensor in a vicinity of a mating zone for the electrical connectors and positioning a connector identification sensor in a vicinity of the electrical connectors. The method includes detecting a presence of the electrical connectors using the connector identification sensor and detecting an audible sound with the audible sensor when the electrical connectors are mated.

DETAILED DESCRIPTION OF THE INVENTION

Figure 1:
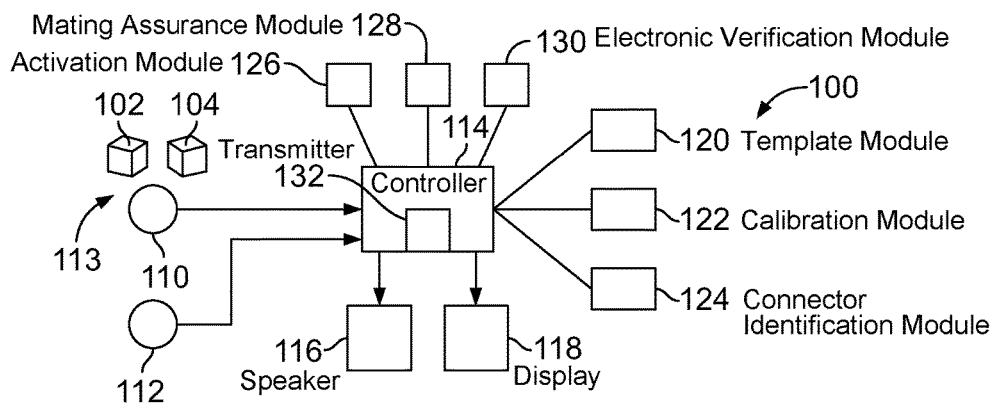
FIG. 1 illustrates a mating assurance system formed in accordance with an exemplary embodiment.

FIG. 1 illustrates a mating assurance system 100 formed in accordance with an exemplary embodiment. The mating assurance system 100 monitors connector mating to provide assurance to the user/system that two components, such as electrical connectors 102, 104, are properly mated. The mating assurance system 100 may provide feedback to an assembler to confirm that the components 102, 104 are properly mated. The mating assurance system 100 may be used for assurance of mating of other types of components in other embodiments, such as for latching of parts other than electrical connectors, such as door panels. While the system is described hereafter in reference to assurance of mating of electrical connectors, the subject matter herein is not intended to be limited to such.

In an exemplary embodiment, the mating assurance system 100 detects an audible sound, such as a latching sound or click, when the electrical connectors 102, 104 are mated. The mating assurance system 100 may use real time signal processing for mating assurance. The mating assurance system 100 provides feedback to the assembler that the electrical connectors 102, 104 are properly mated. The audible verification aspect of the mating assurance system 100 may be used in conjunction with an electronic verification system or other quality control systems that tests the electrical connection between the electrical connectors 102, 104 as a secondary verification system.

In an exemplary embodiment, the mating assurance system 100 identifies the presence of the electrical connector 102 and/or the electrical connector 104, such as using a connector identification module. For example, the mating assurance system 100 may identify the presence by determining that the electrical connector 102 and/or 104 is in or near the assembler's hand or in a mating zone 113. Alternatively or additionally, the mating assurance system 100 may identify the presence by determining the particular type of connector that is present, which may be used to assure that such particular electrical connector 102 and/or 104 has been properly mated. The connector identification module may include one or more connector identification sensors 110 for detecting and/or identifying the presence of the electrical connector 102 and/or 104. Optionally, the connector identification sensor 110 may be worn by the user on a user's body, such as on the user's hand, fingers and/or wrist. The connector identification sensor 110 may be strapped to the assembler's hand or may be integrated into a glove worn by the assembler. As such, the connector identification sensor 110 may be positioned in the vicinity of the electrical connectors 102, 104 and/or the mating zone 113. The connector identification module may include hardware and/or software for identifying the type and/or presence of the electrical connector 102 and/or 104.

Optionally, the mating assurance system 100 may be operated based on inputs and outputs of the connector identification module. For example, the mating assurance system 100 may wait to detect audible sounds until after the system determines that the assembler is grasping the electrical connector 102, 104 and/or until after the system determines that the electrical connector is in the mating zone. As such, the amount of data processing for audible detection may be reduced, which may reduce the number of false detections and/or conserve power, data storage, processor requirements and the like.

Optionally, multiple connector identification sensors 110 may be used. Various types of connector identification sensors 110 may be used depending on the types of electrical connectors 102, 104, the environment the mating assurance system 100 is being used, the sophistication of the mating assurance system 100, the implement housing or holding the connector identification sensor 110, and the like.

The connector identification sensor 110 may be a momentary switch (the momentary switch may be identified as momentary switch 110) that determines the moment(s) that the electrical connector 102, 104 is held by the assembler. For example, such momentary switch may be a push button or other type of switch that is only engaged while it is being depressed, as opposed to a typical "on/off" switch, which is capable of latching into the various set positions. The momentary switch may be normally open or normally closed. For example, when a normally open switch, the momentary switch does not make contact until and unless it is held down, such as when the user is grasping the electrical connector 102, 104. For example, the momentary switch may be provided on the assembler's index finger or thumb (or at another location) such that, when the assembler grasps the electrical connector 102, 104, the momentary switch is pushed closed indicating to the system the presence of the electrical connector 102, 104 (for example, that the assembler is holding the electrical connector 102, 104) and is thus ready to mate the electrical connectors 102, 104. Optionally, other aspects of the mating assurance system 100 (e.g., audible detection) may be off or unusable until the momentary switch identifies the presence of the electrical connectors 102, 104.

The connector identification sensor 110 may be another type of touch based sensor. For example, the connector identification sensor 110 may be a capacitive sensor (the capacitive sensor may be identified as capacitive sensor 110) that determines when the electrical connector 102, 104 is held by the assembler. For example, such capacitive sensor may sense the presence of the electrical connector 102, 104 when the capacitive sensor is capacitively coupled to the electrical connector 102, 104, such as by measuring resistance, impedance or other electrical characteristics. Optionally, the system may use the capacitive sensor to determine when the assembler is grasping the electrical connector 102, 104. In other various embodiments, the system may use the capacitive sensor to determine the type of electrical connector 102, 104 that is being grasped by the user. For example, different types of electrical connectors 102, 104 may have different properties that are sensed differently, such as by varying the type of material, the size of the connector, and the like. The capacitive sensor may be provided on the assembler's index finger or thumb (or at another location) such that, when the assembler grasps the electrical connector 102, 104, the capacitive sensor is capacitively coupled to the electrical connector 102, 104 indicating to the system the presence of the electrical connector 102, 104 and is thus ready to mate the electrical connectors 102, 104. Optionally, other aspects of the mating assurance system 100 (e.g., audible detection) may be off or unusable until the capacitive sensor identifies the presence of the electrical connectors 102, 104.

The connector identification sensor 110 may be another type of sensor, such as a proximity sensor (the proximity sensor may be identified as proximity sensor 110). For example, the connector identification sensor 110 may be an inductive sensor (the inductive sensor may be identified as inductive sensor 110) that determines when the electrical connector 102, 104 is held by the assembler. For example, such inductive sensor may sense the presence of the electrical connector 102, 104 when the inductive sensor is inductively coupled to the electrical connector 102, 104, such as by measuring a magnetic field around the inductive sensor. Optionally, the system may use the inductive sensor to determine when the assembler is grasping the electrical connector 102, 104. In other various embodiments, the system may use the inductive sensor to determine the type of electrical connector 102, 104 that is being grasped by the user. For example, different types of electrical connectors 102, 104 may have different properties that are sensed differently, such as by varying the type of material, the size of the connector, and the like. The inductive sensor may be provided on the assembler's index finger or thumb (or at another location) such that, when the assembler grasps the electrical connector 102, 104, the inductive sensor is inductively coupled to the electrical connector 102, 104 indicating to the system the presence of the electrical connector 102, 104 and is thus ready to mate the electrical connectors 102, 104. Optionally, other aspects of the mating assurance system 100 (e.g., audible detection) may be off or unusable until the inductive sensor identifies the presence of the electrical connectors 102, 104.

The connector identification sensor 110 may be another type of proximity sensor 110. For example, the connector identification sensor 110 may be a radio frequency identification (RFID) sensor (the RFID sensor may be identified as RFID sensor 110) that determines when the electrical connector 102, 104 is held by the assembler. For example, such RFID sensor may sense the presence of an RFID tag associated with the electrical connector 102, 104, such as being located on or in the electrical connector 102, 104 or on the wires extending from the electrical connector 102, 104. Optionally, the system may use the RFID sensor to determine when the assembler is grasping the electrical connector 102, 104. In other various embodiments, the system may use the RFID sensor to determine the type of electrical connector 102, 104 that is being grasped by the user. For example, the RFID tag may identify the particular electrical connector 102, 104 or the particular type of electrical connector 102, 104. The RFID sensor may be provided on the assembler's index finger or thumb (or at another location) such that, when the assembler grasps the electrical connector 102, 104, the RFID sensor senses the RFID tag indicating to the system the presence of the electrical connector 102, 104 and is thus ready to mate the electrical connectors 102, 104. Optionally, other aspects of the mating assurance system 100

(e.g., audible detection) may be off or unusable until the RFID sensor identifies the presence of the electrical connectors 102, 104.

The connector identification sensor 110 may be another type of proximity sensor 110. For example, the connector identification sensor 110 may be a barcode reader (the barcode reader may be identified as barcode reader 110) that determines when the electrical connector 102, 104 is held by the assembler. For example, such barcode reader may sense the presence of a barcode tag associated with the electrical connector 102, 104, such as being located on the electrical connector 102, 104 or on the wires extending from the electrical connector 102, 104. Optionally, the system may use the barcode reader to determine when the assembler is grasping the electrical connector 102, 104. In other various embodiments, the system may use the barcode reader to determine the type of electrical connector 102, 104 that is being grasped by the user. For example, the barcode may identify the particular electrical connector 102, 104 or the particular type of electrical connector 102, 104. The barcode reader may be provided on the assembler's hand, such as at or near the base of the index finger and directed toward the tip of the index finger (or at another location) such that, when the assembler grasps the electrical connector 102, 104, the barcode reader reads the barcode indicating to the system the presence of the electrical connector 102, 104 and is thus ready to mate the electrical connectors 102, 104. The barcode reader may be held by the other hand of the assembler and aimed at the mating zone to identify the presence of the barcode during mating. Optionally, other aspects of the mating assurance system 100 (e.g., audible detection) may be off or unusable until the RFID sensor identifies the presence of the electrical connectors 102, 104.

The mating assurance system 100 includes at least one audible sensor 112 that is located in a vicinity of the mating zone 113 for the electrical connectors 102, 104. In the illustrated embodiment, the audible sensor 112 may be or may include a microphone and may be referred to hereinafter as a microphone 112; however, other types of audible sensors may be used in alternative embodiments, such as any type of audible sensor capable of detecting the audible click made when the electrical connectors 102, 104 are mated. Any number of microphones 112 may be used in various embodiments. The microphone 112 may be an omnidirectional microphone.

Optionally, when multiple microphones 112 are used, the microphones 112 may be positioned at different distances from the mating zone 113, such that the various microphones 112 receive the audible sound at different times (e.g., the second microphone may be positioned further from the electrical connectors 102, 104 such that the audible sound made when the electrical connectors 102, 104 are mated is received at a later time at the second microphone as compared to the first microphone). The mating assurance system 100 may use the time difference in audible detection to determine the relative distances between the microphones 112 and the electrical connectors 102, 104 and/or to determine a direction of sound origination (e.g., the direction of the mating zone 113).

Using multiple microphones 112 may enhance reliability of the sound detection of the mating assurance system 100 as compared to systems that use a single microphone. Using multiple microphones 112 may reduce the probability of false positive identification of connector mating as compared to systems that use a single microphone. Using multiple microphones 112 allows collecting audio signals from different angles to provide enhanced signal signature matching capabilities and/or for determining angular orientation of the electrical connectors 102, 104 when mated. Optionally, the mating zone 113 may be positioned beyond the first microphone 112 such that the first microphone 112 is positioned between the mating zone 113 and the second microphone 112. In other embodiments, the mating zone 113 may be positioned between the first and second microphones 112. The mating zone 113 may be staggered forward of, rearward of, or to one side or the other of the first microphone 112 and/or the second microphone 112.

The microphone 112 and the connector identification sensor 110 are connected to one or more controller(s) 114. The controller 114 receives audio signals from the microphone 112 and receives connector identification signals from the connector identification sensor 110. The microphone 112 and connector identification sensor 110 may be connected to the controller 114 by wired or wireless connections. The controller 114 can include or represent hardware circuitry that includes and/or is connected with one or more processors (e.g., microprocessors, integrated circuits, application specific integrated circuits, field programmable gate arrays, or other electronic logic-based devices) that operate to perform one or more, or all, of the operations described herein.

The controller 114 processes the audio signals and/or the connector identification signals for mating assurance. The controller 114 may provide feedback to the assembler based on the connector identification signals and/or the audio signals. The controller 114 may process the connector identification signals separate from the audio signals. The controller 114 may process the connector identification signals and/or the audio signals by transmitting the connector identification signals and/or the audio signals to another controller or processing unit. For example, the controller 114 may be a user worn controller, which may be worn on a user's body, such as on the user's wrist. Such controller 114 may perform some processing and may send the connector identification signals and/or the audio signals and/or the processed signals or data to a main controller, such as a workstation or other computer where the signals may be further processed and/or stored. Additionally, signals or data may be transmitted from the main controller to the user worn controller 114.

In an exemplary embodiment, the controller 114 identifies the presence of the electrical connectors 102, 104 based on the connector identification signals from the connector identification sensor(s) 110. The controller 114 may identify the presence of the electrical connectors 102, 104 by determining when the connector identification sensor 110 is in the vicinity of the electrical connectors 102, 104 and/or when the connector identification sensor 110 touches the electrical connectors 102, 104 based on the connector identification signals. The controller 114 may identify the presence of the electrical connectors 102, 104 by determining the type of electrical connectors 102, 104, such as through proximity sensing, capacitive sensing, inductive sensing, RFID reading, barcode reading or by other processes. Optionally, the controller 114 may not begin audible signal processing until after the controller 114 positively identifies the presence of the electrical connectors 102, 104 (for example, after the controller 114 determines that the assembler is grasping the electrical connectors 102, 104). As such, battery power, processing power, memory, and the like of the controller 114 or other components of the mating assurance system 100 may be preserved.

The controller 114 determines if the electrical connectors 102, 104 are properly mated based on the audio signals as a form of audible verification of proper mating. In an exemplary embodiment, the controller 114 compares the audio signals from the microphone 112 to templates or characteristic signatures for mating assurance. When multiple microphones 112 are used, the controller 114 may compare the time of receipt of the audio signals from the microphones 112 during processing.

The controller 114 determines or verifies if the audible sound received at the microphone 112 originated from mating of the electrical connectors 102, 104 and/or filters out the audio signals if it is determined that the audible sound was from a source other than the mating of the electrical connectors 102, 104. For example, the controller 114 may filter background noise if the filter determines that the audible sound was from a source other than the mating of the electrical connectors 102, 104, which may enhance the audible sound for the assembler. For example, by using multiple microphones 112, the controller 114 may determine the direction of origin of the audible sound and may filter out audible sounds that are determined to occur from a direction outside of the mating zone 113, such as from a direction behind the second microphone 112 or from a direction too remote from the mating zone 113 to be occurring from the mating of the electrical connectors 102, 104. The mating assurance system 100 may include other microphones in or around the mating zone 113 that listen for background noise and the controller 114 may compare the audio signals from each of the microphones to isolate the audible sounds associated with mating the electrical connectors 102, 104 from the background noise. The controller 114 may have other means of filtering the background noise detected by the microphones.

In an exemplary embodiment, the microphone 112 may be held by the assembler proximate to the assembler's hand. For example, the microphone 112 may be part of a wearable electronic, such as part of a strap, band or clip held on the assembler's hand or integrated as part of a glove worn by the assembler. In one particular embodiment, the microphone 112 may be worn by the assembler at or near the assembler's fingers, at or near the assembler's wrist, or otherwise and thus may be positioned at or near the mating zone 113 near enough to the electrical connectors 102, 104 to detect the audible sounds of mating. Optionally, the microphone 112 may physically engage the electrical connectors 102, 104 such that the latching sound is transmitted through the structure of the electrical connectors 102, 104 directly into the microphone 112. In other embodiments, rather than being worn by the assembler, the microphone 112 may be fixed or mounted in a particular location within the mating zone 113 in the vicinity where the assembler is mating the electrical connectors 102, 104.

In an exemplary embodiment, the mating assurance system 100 may be adapted for use in an area where visibility of and accessibility to the mating zone 113 is limited. For example, the electrical connectors 102, 104 may be part of wire harnesses that are assembled and mated during assembly of a car in an automotive plant. The electrical connectors 102, 104 may be mated in an area under the hood, behind the engine, behind the dashboard, under a seat, or in other difficult to see areas, making use of the audible clicking sound when the electrical connectors 102, 104 are mated. The mating assurance system 100 enhances the audible sound providing various types of feedback to the assembler to ensure that the electrical connectors 102, 104 are properly mated. Additionally, the mating of the electrical connectors 102, 104 may occur in a noisy environment, such as in an assembly plant, manufacturing plant or elsewhere where the audible click made when the latching of the electrical connectors 102, 104 may be unheard by the assembler. Optionally, one of the connectors, such as the electrical connector 104 may be integrated into another component, such as a header or electronic module that is permanently mounted into the vehicle and thus is not movable by the assembler. In such cases, only the other electrical connector 102 is grasped by the user and mated to the permanent electrical connector 104.

Figure 2:
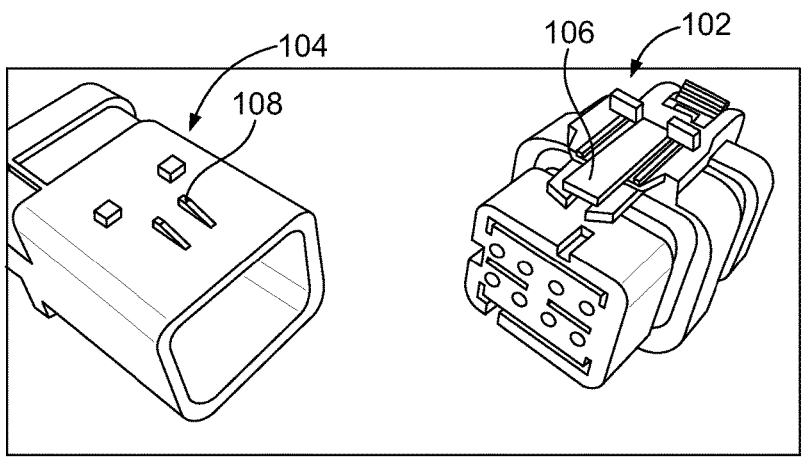
FIGS. 2 and 3 illustrate exemplary embodiments of different types of electrical connectors.
Figure 3:
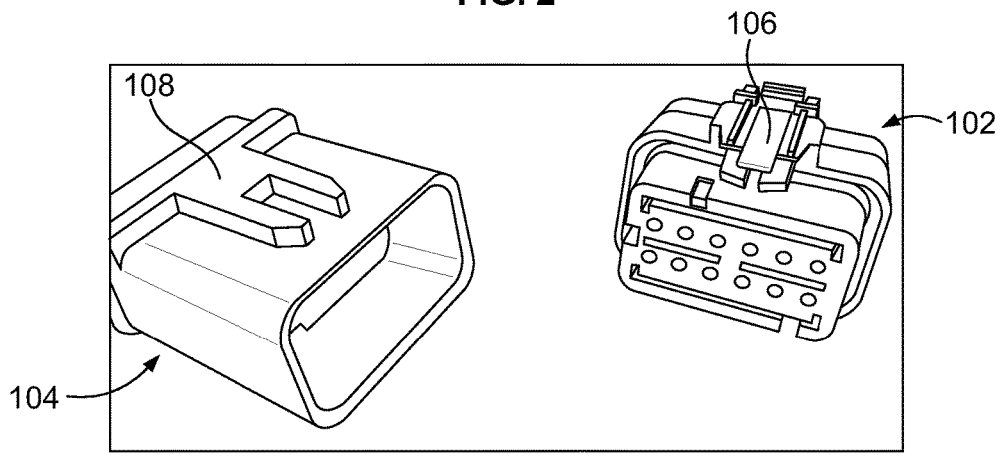

The electrical connectors 102, 104 may be any type of electrical connectors. In an exemplary embodiment, the mating assurance system 100 may be used during assembly of automotive electrical connectors. The electrical connectors 102, 104 may be sealed or unsealed automotive connectors; however are not intended to be limited to such. FIGS. 2 and 3 illustrate exemplary embodiments of different types of electrical connectors 102, 104. For example, FIG. 2 illustrates an eight position header and an eight position receptacle having eight contacts and associated wires extending therefrom. The electrical connectors 102, 104 illustrated in FIG. 3 are twelve position header and receptacle connectors having twelve contacts and associated wires. Other types of electrical connectors 102, 104 may be provided in alternative embodiments, such as two position connectors, four position connectors, six position connectors, ten position connectors, fourteen position connectors, and the like. Other types of electrical connectors 102, 104 other than rectangular connectors, such as circular connectors, may be provided in other alternative embodiments. The electrical connectors 102 and/or 104 may be board mounted connectors rather than being cable or wire connectors, such as a header connector that is integrated or coupled to equipment or components within the vehicle. The connectors may have different types or sized latches having different audible characteristics during latching.

The mating assurance system 100 may be used for connector identification purposes, such as to identify latching of the eight position connectors as compared to the twelve position connectors (or other types of connectors). The mating assurance system 100 may be used to identify the mating orientation of the electrical connectors 102, 104, such as to determine if the electrical connectors 102, 104 are top-up, bottom-up, side-up and the like as the audible characteristics of the latching sound or click may be different based on the orientation of the electrical connectors 102, 104. Additionally, the connector identification sensor 110 may be used to determine the orientation of the electrical connectors 102, 104. The mating assurance system 100 may have different templates for the various orientations for enhanced signal processing.

The header electrical connectors 102 include a deflectable latch 106 and the receptacle electrical connectors 104 include a catch 108 for the latch 106, or vice versa. Optionally, the latch 106 of the twelve position header connector (FIG. 3) may be different than the latch 106 of the eight position header electrical connector 102 (FIG. 2). For example, the latches 106 may have different lengths, may be made of different materials, may have different shapes, and the like. The catches 108 may have different sizes, shapes, number of teeth, and the like. The different latches 106 and/or catches 108 have different audio signatures when latching to the corresponding catches 108. For example, when the latch 106 engages the catch 108 an audible click may be made, such as when the latch 106 snaps down into position behind the catch 108 (or multiple clicks may be heard when multiple teeth are provided). The latch 106 and/or catch 108 may be designed to have prominent audio signatures. Providing different latches 106 and/or catches 108 provides different audio signatures when the electrical connectors 102, 104 are mated. The mating assurance system 100 may be configured to differentiate between the different audio signatures of the different types of electrical connectors 102, 104 to identify the particular electrical connectors 102, 104 that are mated. Additionally, the audible sound produced when the latches 106 engage the corresponding catches 108 may have different audible characteristics depending on the orientation of the latches 106 or catches 108 108 relative to the microphones 112, 112 (e.g., on the top surface facing the microphones versus on the bottom with the assemblers hand between the microphones and the latches/catches). The mating assurance system 100 may be able to differentiate when the electrical connectors 102, 104 are in different orientations.

The connector identification sensor 110 may be used to identify and distinguish between the different types of electrical connectors 102, 104 (for example, between the eight position and the twelve position connectors). For example, the connector identification sensor 110 may use capacitive sensing, inductive sensing, RFID sensing, barcode sensing, or other types of sensing to determine the type of electrical connector 102, 104.

Returning to FIG. 1, the connector identification sensor 110 detects the presence of the electrical connectors 102, 104 either in the user's grasp or in the mating zone 113. The connector identification signals are transmitted to the controller 114. The controller 114 processes the connector identification signals and provides an output to another portion of the controller 114, to another controller 114 and/or provides feedback to the assembler. The audible sensor 112 detects the latch click(s) that occurs when the latch 106 is latched, signifying that the electrical connectors 102, 104 are properly mated. The audio signals, including the audio signals corresponding to the latch click, are transmitted to the controller 114. The controller 114 processes the audio signals and provides an output to another portion of the controller 114, to another controller 114 and/or provides feedback to the assembler.

In an exemplary embodiment, the controller 114 provides audible feedback to the assembler based on the audio signals. For example, a speaker 116 may be coupled to the controller 114 and output from the controller 114 may cause the speaker 116 to provide audible feedback. The speaker 116 may enhance (e.g., make louder) the click detected by the microphone 112 to make it easier or possible for the assembler to hear. The audible feedback may be based on the connector identification signals, such as a sound when the presence of the electrical connectors 102, 104 is detected. The controller 114 may provide other types of feedback, such as tactile feedback to the user, which may be in the form of vibration.

In an exemplary embodiment, the controller 114 provides visual feedback to the assembler at a display 118 associated with the controller 114. The visual feedback may be based on the connector identification signals, such as a visual indication when the presence of the electrical connectors 102, 104 is detected. The display 118 may include LEDs or may include a display screen. The display 118 may be worn by the user. Alternatively, the display 118 may be a stationary monitor, such as a monitor setting on a desk, integrated into a computer or other system, or mounted to a wall, or may be a portable monitor. The display 118 may display visual confirmation that proper mating has occurred based on the audio signals processed by the controller 114, such as by displaying a particular color, displaying a particular icon, displaying words and/or symbols, and the like.

The controller 114 may determine the type of the electrical connectors 102, 104 mated (e.g., eight position versus twelve position versus another type) and may display information relating to the particular type of electrical connectors 102, 104 that have been mated. For example, during a particular assembly, the assembler may need to mate a four position connector, an eight position connector and a twelve position connector. After the assembler performs the mating, the assembler may refer to the display 118 to verify that all three connectors where mated. The display 118 may indicate that only two of the connectors were actually mated, causing the assembler to return to the vehicle and figure out which connector was not properly mated. Alternatively, the controller 114 may identify which of the connectors were mated based on the audio signals and indicate on the display 118 which of the three connectors were properly mated and/or which of the three connectors were not properly mated. The controller 114 may identify which of the connectors were handled by the assembler, such as based on the connector identification signals, and may also identify which of the connectors were properly mated, such as based on the audible signals.

In an exemplary embodiment, the controller 114 may include or be coupled to a template module 120 that includes different type templates of different types of electrical connectors 102, 104 (e.g., 2 position, 4 position, 6 position, 8 position, 12 position, etc.). The template module 120 may include audio signatures of the various types of electrical connectors 102, 104. The template module 120 may include connector identification signatures of the various types of electrical connectors 102, 104, which may include capacitive signatures, inductive signatures, RFID signatures, barcode signatures, or other types of signatures to determine the type of electrical connector 102, 104. The template module 120 may include different orientation templates of signatures of the various electrical connectors 102, 104 at different orientations (e.g., top-up, bottom-up, side-up and the like).

The controller 114 may compare the received connector identification signal and/or audio signal to the various templates to determine which type of electrical connectors 102, 104 was mated and/or the orientation of the electrical connectors 102, 104 in the mating zone 113 when mated. For example, the template module 120 may have different time domain characteristics and/or frequency domain characteristics for the different types of electrical connectors 102, 104 and/or for the different orientations. The controller 114 may correlate the signals against time domain templates and/or frequency domain templates to identify the particular type of electrical connectors 102, 104 that are mated and/or to determine the orientation of the electrical connectors 102, 104 during mating. Having different orientation templates allows the system to account for different connector identification characteristics or different audible characteristics of the latching when a particular electrical connector type is mated, which may lead to a false-negative determination in systems that do not include multiple orientation templates.

In an exemplary embodiment, the controller 114 may include or be coupled to a calibration module 122 that is used to calibrate the controller 114 and/or the template module 120. For example, in a calibration mode, the electrical connectors 102, 104 may be mated, preferably numerous times and/or in various orientations to increase the amount of data to calibrate the controller 114 and/or template module 120. Time domain characteristics, frequency domain characteristic and/or other characteristics of the audio signal associated with the mating (e.g. the click) detected by the microphone 112 may be recorded and a median or average time domain template, frequency domain template and/or other type of template may be determined for each type of electrical connector 102, 104 (e.g., 2 position, 4 position, 6 position, 8 position, 12 position, etc.) that may be assembled and monitored by the mating assurance system 100. The controller 114 may be calibrated and programmed for use with any number of different types of electrical connectors 102, 104. Based on the unique signatures of the audible sound made when the particular types of electrical connectors 102, 104 are mated and/or when the particular electrical connectors 102, 104 are mated at various orientations, the controller 114 is able to identify and determine exactly which type of electrical connectors 102, 104 have been mated at any particular time. The controller 114 provides feedback at the display 118 for the assembler to identify which types of electrical connectors 102, 104 have been mated.

In an exemplary embodiment, the controller 114 includes a connector identification module 124. The connector identification module 124 receives the connector identification signals from the connector identification sensor 110. The connector identification module 124 processes the connector identification signals, such as by comparing the connector identification signals to the templates to identify the presence of the electrical connector 102, 104 based on the connector identification signals from the connector identification sensor(s) 110. The connector identification module 124 may identify the presence of the electrical connectors 102, 104 by determining when the connector identification sensor 110 is in the vicinity of the electrical connectors 102, 104 and/or when the connector identification sensor 110 touches the electrical connectors 102, 104 based on the connector identification signals. The connector identification module 124 may identify the presence of the electrical connectors 102, 104 by determining the type of electrical connectors 102, 104, such as through proximity sensing, capacitive sensing, inductive sensing, RFID reading, barcode reading or by other processes.

In an exemplary embodiment, the controller 114 includes an activation module 126. The activation module 126 may activate various components of the mating assurance system 100 and/or may deactivate various components of the mating assurance system 100. For example, the activation module 126 may activate or deactivate (e.g., turn on/off, place in sleep/awake mode, and the like) the various components to conserve battery usage, processing usage, memory usage, and the like. Optionally, the activation module 126 receives the connector identification signals form the connector identification sensor 110 or from the connector identification module 124. When the activation module 126 determines that the electrical connectors 102, 104 are grasped by the user or in the vicinity of the mating zone 113, the activation module 126 may activate the audible sensor 112 and/or a mating assurance module 128 of the controller 114. Optionally, the audible sensor 112 and/or a mating assurance module 128 may be activated for a predetermined period of time after the electrical connector 102, 104 presence is detected. Optionally, the activation module 126 may deactivate the audible sensor 112 and/or a mating assurance module 128 after such predetermined time. As such, the audible processing, data storage, and component usage may be reduced, which may conserve battery usage, memory usage, data processing, and the like.

The mating assurance module 128 receives the audible signals from the audible sensor 112. The mating assurance module 128 processes the audible signals, such as by comparing the audible signals to the templates to identify the "click" or other sound associated with connector mating. The mating assurance module 128 processes the audio signals and provides an output to another portion of the controller 114, to another controller 114 and/or provides feedback to the assembler.

The mating assurance module 128 may record data and/or process data over time. The mating assurance module 128 detects events, which may correspond to latching or mating of the connectors. False events may occur when the microphone touches something, when the connectors touch some other component, such as if the connectors are touched together but not mated or if the connectors are dropped, when other noises occur in the assembly facility, such as using other tools or machines around the assembly factory, and the like. The false events may be identified by the mating assurance module 128, such as by analyzing the audio signatures and comparing the audio signatures to the templates. The mating assurance module 128 may ignore false event noises. The proper mating events (e.g., click) may be verified by comparing the audio signatures of the recorded data to the templates, such as time domain templates and/or frequency domain templates. When an event is detected, the controller 114 may provide audible, visual or other feedback outputs to the assembler to confirm that the connectors are properly mated.

In an exemplary embodiment, the controller 114 includes or is electrically connected to an electronic verification module 130. The electronic verification module 130 sends signals through the electrical connectors 102, 104 to verify that the electrical connectors 102, 104 are electrically connected. The controller 114 may verify which electrical connectors 102, 104 have affirmatively passed the electronic verification module 130 and compare such list of electrical connectors 102, 104 with the list of electrical connectors 102, 104 that have affirmatively passed audible verification. Data from the controller 114 and/or electronic verification module 130 may be sent to a master quality control database or system on the vehicle or at the assembly plant for review and/or verification of successful assembly of the electrical connectors 102, 104. Such information may be combined with information from other modules or systems.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), a given module or unit may be added, or a given module or unit may be omitted. For example, some or all of the various modules 120-130 may be integrated with the controller 114. For example, components of the various modules 120-130 and the controller 114 may be implemented on one or more circuit boards and/or may be housed within a common housing. The various modules 120-130 may have inputs and/or outputs that are transmitted to other modules 120-130 and/or to the controller 114. The controller 114 may have a transmission module or transmitter 132 that may transmit and/or receive signals, data and the like to other components, such as another controller, computer, workstation, and the like.

It should be noted that the various embodiments may be implemented in hardware, software or a combination thereof. The various embodiments and/or components, for example, the units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer" and "controller" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "controller" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

Figure 4:
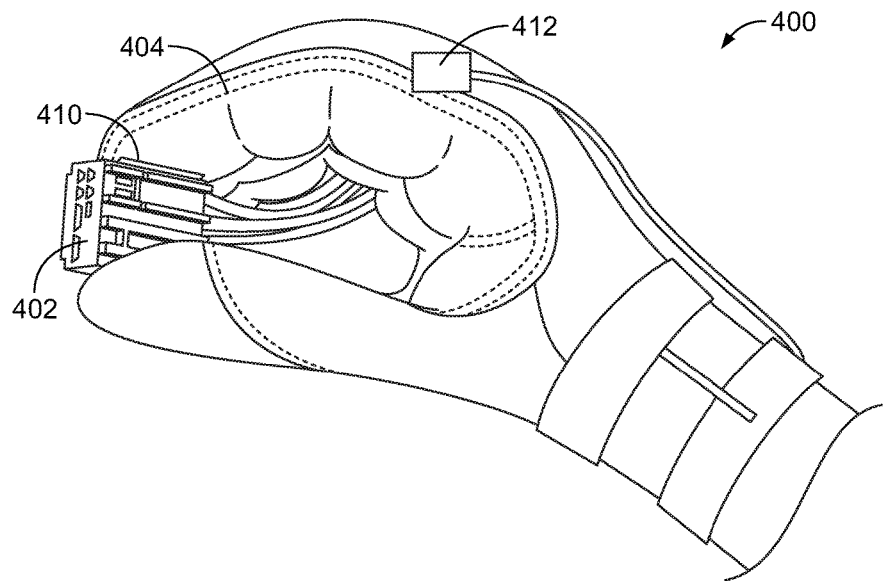
FIG. 4 illustrates a mating assurance system formed in accordance with an exemplary embodiment.

FIG. 4 illustrates a mating assurance system 400 formed in accordance with an exemplary embodiment. The mating assurance system 400 provides connector identification and audible verification of mating to an assembler to confirm that an electrical connector 402 is properly mated, such as to another electrical connector. In an exemplary embodiment, the mating assurance system 400 identifies the presence of the electrical connector 402, such as using a connector identification sensor 410 and the mating assurance system 400 detects an audible sound when the electrical connector 402 is mated, such as using an audible sensor 412.

In the illustrated embodiment, the connector identification sensor 410 is a momentary switch provided at or near the finger tip of the assembler. The audible sensor 412 is a microphone provided at or near the base of the index finger of the assembler. For example, the momentary switch 410 may be integrated into or strapped onto a glove 404 worn by the user. The microphone 412 may be integrated into or strapped onto the glove 404. The components 410, 412 may be otherwise positioned within a mating zone in the vicinity where the assembler is mating the electrical connector 402. The connector identification sensor 410 and the audible sensor 412 may be electrically connected to a controller, such as the controller 114 (shown in FIG. 1).

Figure 5:
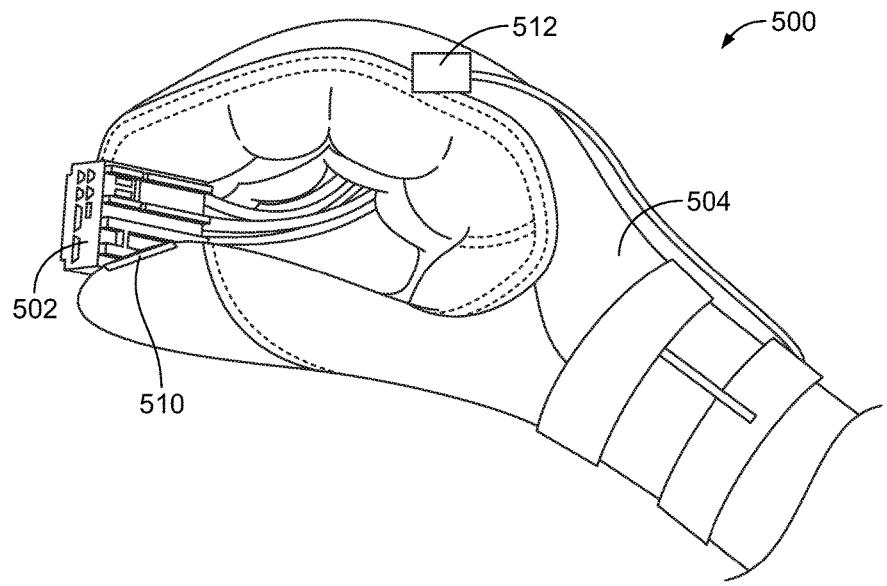
FIG. 5 illustrates a mating assurance system formed in accordance with an exemplary embodiment.

FIG. 5 illustrates a mating assurance system 500 formed in accordance with an exemplary embodiment. The mating assurance system 500 provides connector identification and audible verification of mating to an assembler to confirm that an electrical connector 502 is properly mated, such as to another electrical connector. In an exemplary embodiment, the mating assurance system 500 identifies the presence of the electrical connector 502, such as using a connector identification sensor 510 and the mating assurance system 500 detects an audible sound when the electrical connector 502 is mated, such as using an audible sensor 512.

In the illustrated embodiment, the connector identification sensor 510 is a proximity switch provided at or near the finger tip of the assembler, such as on the thumb. The proximity sensor 510 may be used in connection with a momentary switch, such as the momentary switch 410 (shown in FIG. 4). The proximity sensor 510 may be integrated into or strapped onto a glove 504 worn by the user. Optionally, the proximity sensor 510 may be an inductive sensor, a capacitive sensor, an RFID reader or another type of proximity sensor 510. Optionally, when the proximity sensor is an RFID reader 510, the connector may include an RFID tag or other component on the surface of the connector 502, embedded in the connector 502, or part of the wire(s) extending from the connector 502, which is read or sensed by the RFID reader 510.

The audible sensor 512 is a microphone provided at or near the finger tip of the assembler. Providing the microphone 512 closer to the electrical connector 502 (as compared to the position shown in FIG. 4) may enhance the audible click sound made during mating. The microphone 512 may be integrated into or strapped onto the glove 504. The components 510, 512 may be otherwise positioned within a mating zone in the vicinity where the assembler is mating the electrical connector 502. The connector identification sensor 510 and the audible sensor 512 may be electrically connected to a controller, such as the controller 114 (shown in FIG. 1).

Figure 6:
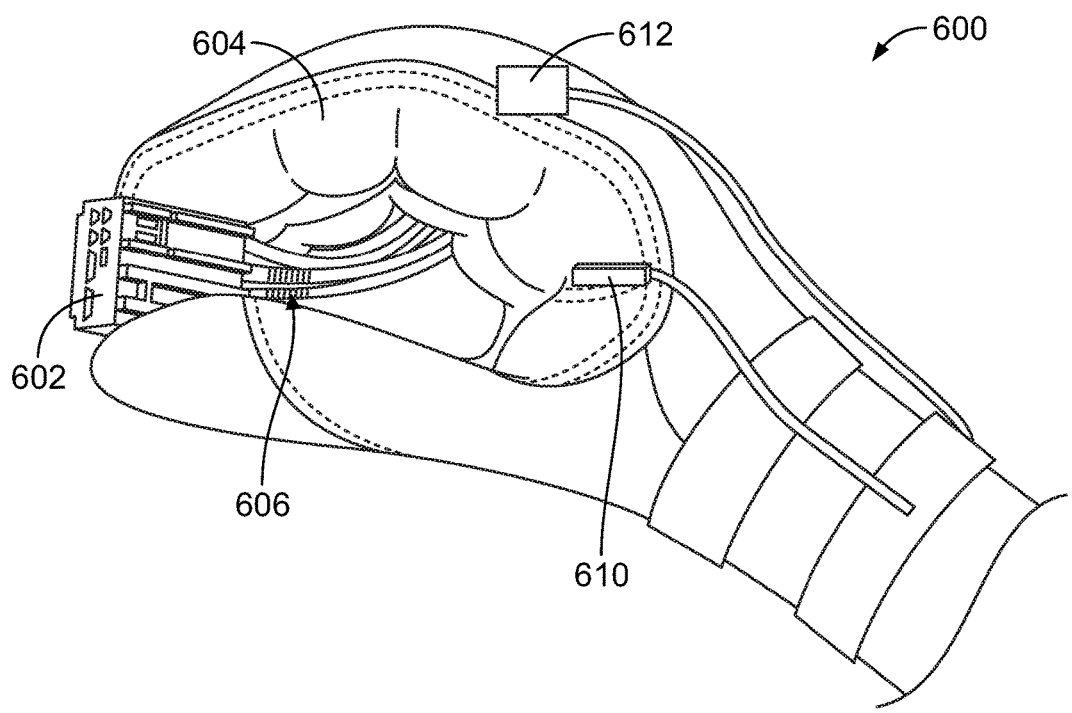
FIG. 6 illustrates a mating assurance system formed in accordance with an exemplary embodiment.

FIG. 6 illustrates a mating assurance system 600 formed in accordance with an exemplary embodiment. The mating assurance system 600 provides connector identification and audible verification of mating to an assembler to confirm that an electrical connector 602 is properly mated, such as to another electrical connector. In an exemplary embodiment, the mating assurance system 600 identifies the presence of the electrical connector 602, such as using a connector identification sensor 610 and the mating assurance system 600 detects an audible sound when the electrical connector 602 is mated, such as using an audible sensor 612.

In the illustrated embodiment, the connector identification sensor 610 is a barcode reader provided at or near the base of the index finger of the assembler. The barcode reader 610 may be used in connection with a momentary switch, such as the momentary switch 410 (shown in FIG. 4). Optionally, when the momentary switch detects the presence of the electrical connector 602, the system may activate the barcode reader 610. For example, an activation module of a controller may cause the barcode reader 610 to activate when the user grasps the electrical connector 602. The barcode reader 610 may be integrated into or strapped onto a glove 604 worn by the user such that the barcode reader 610 is able to view the electrical connector 602 and read a barcode 606 on the electrical connector 602 (e.g., on the wires). The audible sensor 612 is a microphone provided in the vicinity of the mating zone. The components 610, 612 may be otherwise positioned within a mating zone in the vicinity where the assembler is mating the electrical connector 602. The connector identification sensor 610 and the audible sensor 612 may be electrically connected to a controller, such as the controller 114 (shown in FIG. 1).

To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A connector mating assurance system comprising:
an audible sensor configured to be located in a vicinity of a mating zone for electrical connectors, the audible sensor configured to detect an audible sound when the electrical connectors are mated; and
a connector identification sensor configured to be located in the vicinity of the electrical connectors, the connector identification sensor configured to identify the presence of the electrical connectors separate from the audible sensor; and
a controller connected to the audible sensor and the connector identification sensor, the controller receiving connector identification signals from the connector identification sensor, the controller receiving audio signals from the audible sensor, the controller processing the connector identification signals and the audio signals for mating assurance.

2. The connector mating assurance system of claim 1, wherein the controller only processes the audio signals after the controller positively identifies the electrical connectors based on the connector identification signals.

3. The connector mating assurance system of claim 1, wherein the controller processes the connector identification signals to determine a type of electrical connector sensed by the connector identification sensor.

4. The connector mating assurance system of claim 1, wherein the audible sensor and the connector identification sensor are worn by a user on or near the user's hand.

5. The connector mating assurance system of claim 1, wherein the controller provides feedback to the user based on at least one of the connector identification signals and the audio signals.

6. The connector mating assurance system of claim 1, wherein the connector identification sensor comprises a momentary switch configured to detect when the user is grasping the electrical connector.

7. The connector mating assurance system of claim 6, wherein the controller processes the audio signals only when the momentary switch is activated and the user is grasping the electrical connector.

8. The connector mating assurance system of claim 1, wherein the controller determines when the connector identification sensor is in the vicinity of the electrical connector and processes the audio signals after the controller detects that the connector identification sensor is in the vicinity of the electrical connector.

9. The connector mating assurance system of claim 8, wherein the controller processes the audio signals for a predetermined time after the controller initially detects that the connector identification sensor is in the vicinity of the electrical connector.

10. The connector mating assurance system of claim 1, wherein the connector identification sensor comprises a proximity sensor configured to detect when the electrical connector is in a vicinity of the proximity sensor to identify the electrical connector.

11. The connector mating assurance system of claim 10, wherein the proximity sensor is an inductive sensor inductively sensing the electrical connector to identify the presence of the electrical connector.

12. The connector mating assurance system of claim 10, wherein the proximity sensor is a capacitive sensor capacitively sensing the electrical connector to identify the presence of the electrical connector.

13. The connector mating assurance system of claim 1, wherein the connector identification sensor comprises a barcode reader configured to read a barcode on the electrical connector or a wire extending from the electrical connector to identify the type of electrical connector.

14. The connector mating assurance system of claim 1, wherein the connector identification sensor comprises an RFID reader configured to read an RFID tag on the electrical connector to identify the type of electrical connector.

15. The connector mating assurance system of claim 1, wherein the audible sensor detects the audible sound that occurs when a latch of one electrical connector latches to the corresponding other electrical connector.

16. The connector mating assurance system of claim 1, wherein the connector identification sensor is discrete from the audible sensor and identifies the presence of the electrical connectors without detecting an audible sound.

17. A connector mating assurance system comprising:
    a user worn sensor unit configured to be worn on or near a user's hand, the user worn sensor unit comprising an audible sensor and a connector identification sensor discrete from the audible sensor and configured to be positioned in a vicinity of a mating zone for electrical connectors, the audible sensor configured to detect an audible sound when the electrical connectors are mated, the connector identification sensor configured to identify the presence of the electrical connectors without detecting an audible sound; and
    a controller connected to the audible sensor and the connector identification sensor, the controller receiving connector identification signals from the connector identification sensor, the controller receiving audio signals from the audible sensor, the controller processing the connector identification signals and the audio signals for mating assurance.

18. A method of detecting electrical connector mating, the method comprising:
    positioning an audible sensor in a vicinity of a mating zone for the electrical connectors;
    positioning a connector identification sensor in a vicinity of the electrical connectors, the connector identification sensor being separate from the audible sensor;
    communicatively coupling the audible sensor to a controller to receive audio signals from the audible sensor and communicatively coupling the connector identification sensor to the controller to receive connector identification signals from the controller;
    processing the connector identification signals using the controller for detecting a presence of the electrical connectors using the connector identification sensor; and
    processing the audio signals using the controller for detecting an audible sound with the audible sensor when the electrical connectors are mated.

19. The method of claim 18, wherein said processing the connector identification signal comprises processing the connector identification signal to determine that a user is grasping the electrical connector.

20. The method of claim 18, wherein said processing the connector identification signal comprises processing the connector identification signal to determine a type of electrical connector being grasped by a user.

21. The method of claim 18, wherein said positioning an audible sensor and said positioning a connector identification sensor comprises positioning an audible sensor and a connector identification sensor on a glove worn by a user.

* * * * *